United States Patent [19]
Armbruster

[11] Patent Number: 6,034,070
[45] Date of Patent: Mar. 7, 2000

[54] TREATMENT OF VIRAL DISEASE IN SWINE

[75] Inventor: Gregory Alan Armbruster, Maple Grove, Minn.

[73] Assignee: Eli Lilly and Company, Indianapolis, Ind.

[21] Appl. No.: 09/259,780

[22] Filed: Mar. 1, 1999

Related U.S. Application Data

[60] Provisional application No. 60/076,466, Mar. 2, 1998.

[51] Int. Cl.[7] .................................................. A61K 31/70
[52] U.S. Cl. ............................................................. 514/30
[58] Field of Search ................................................. 514/30

[56] References Cited

U.S. PATENT DOCUMENTS

| | | | |
|---|---|---|---|
| 4,820,695 | 4/1989 | Debono et al. | 514/30 |
| 5,574,020 | 11/1996 | Klink et al. | 514/30 |

*Primary Examiner*—Raymond Henley, III
*Attorney, Agent, or Firm*—Frederick D. Hunter

[57] ABSTRACT

The invention is directed to the use of tilmicosin and other compounds of U.S. Pat. No. 4,820,695 for the treatment of viral infection in swine.

16 Claims, No Drawings

TREATMENT OF VIRAL DISEASE IN SWINE

CROSS REFERENCE

This application claims priority of Provisional Application Ser. No. 60/076,466, filed Mar. 2, 1998.

BACKGROUND OF THE INVENTION

U.S. Pat. No. 4,820,695 describes certain macrolide antibiotics. Using the description of U.S. Pat. No. 4,820,695, such a compound may be described as a compound of formula I:

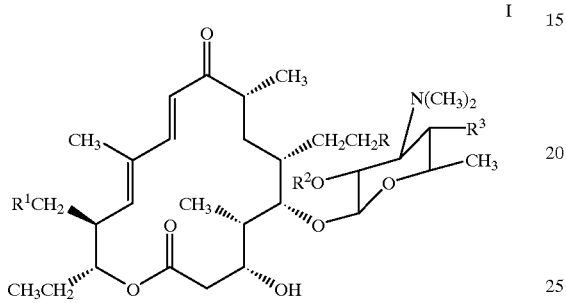

wherein

R is a saturated or unsaturated secondary amino group of the formula

in which the nitrogen atom is part of an otherwise carbocyclic ring system selected from a monocyclic ring containing from 5 to 16 ring atoms or a bicyclic or tricyclic ring system containing from 8 to 20 ring atoms or such a group wherein one or more of the carbon atoms is substituted by $C_1$–$C_4$ alkyl, $C_2$–$C_4$ alkenyl, $C_1$–$C_3$ alkoxy, $C_1$–$C_4$ alkoxycarbonyl, hydroxyl, $C_1$–$C_4$ alkanoyloxy, halo, halo-$C_1$–$C_4$ alkyl, —N($C_1$–$C_4$ alkyl)$_2$, —N(CH$_2$)$_m$,

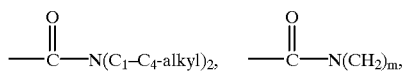

cyano, ethylenedioxy, benzyl, phenyl, or phenyl substituted by from 1 to 3 substituent—substituents selected from nitro, halo, $C_1$–$C_4$-alkyl, $C_1$–$C_4$ alkoxy, hydroxy, amino, or mono- or di-($C_1$–$C_4$ alkyl) amino;

m is an integer from 4 through 7;

$R^1$ is

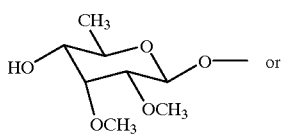

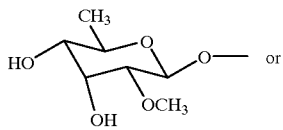

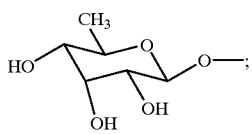

$R^2$ is hydrogen; $C_1$–$C_5$-alkanoyl or $C_1$–$C_5$-alkanoyl having from one to three halo substituents; benzoyl, phenylacetyl or phenylprionyl or benzoyl, phenylacetyl or phenylpropionyl having from one to five halo or methyl or from one to two methoxyl, nitro or hydroxyl substituents;

$R^3$ is hydroxy; $C_1$–$C_5$ alkanoyloxy; $C_1$–$C_5$-alkanoyloxy having from one to three halo substituents; benzoyloxy, phenylacetoxy or phenoxyacetoxy or benzoyloxy, phenylacetoxy or phenoxyacetoxy having from one to five halo or methyl or from one to two methoxyl, nitro or hydroxyl substituents; or

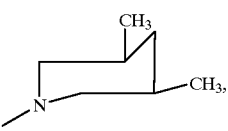

or an acid addition salt thereof.

A particularly useful formula I compound is one wherein R is

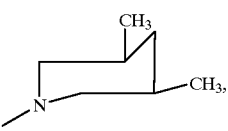

$R_1$ is an (a) group, $R^2$ is H and $R^3$ is hydroxy. It is known by the non-proprietary name tilmicosin, assigned by USAN, the United States Adopted Names organization. It has the following structural formula:

BRIEF SUMMARY OF THE INVENTION

It has now been discovered, and this is an aspect of the present invention, that a compound of formula I, and tilmicosin in particular, can be used to control certain virus infections in swine. A compound of formula I may be used as such or in the form of a physiologically acceptable salt.

Known viruses which are pathogenic in mammal species are of large numbers; but there are a few which present a most severe challenge to the swine industry, including Swine Infertility and Respiratory Syndrome Virus (SIRSV), also known as Porcine Respiratory and Reproductive Syndrome Virus (PRRSV), referred to hereafter as SIRSV; Lelystad Virus, as seen in European swine populations; and a rare disease, Swine Abortion Mortality Syndrome Virus, referred to hereafter as SAMSV, thought to be a variant of SIRSV.

Swine Infertility and Respiratory Syndrome was first described in the United States in 1987. The condition was characterized by abortion, premature farrowing, stillborn pigs, and respiratory disease with death loss and chronic poor performance of nursing and weaned pigs. The severity of clinical signs in a herd depends on many factors including stress, concurrent disease, herd management, and virulence of the specific SIRSV strain. The virus can infect swine at any stage of life; as a nursery pig, finishing pig, boar, or breeding female. The history of the condition indicates that it appeared in Europe at about the same time as in the U.S. The European clinical signs are also caused by a strain of an arterivirus, commonly known as the Lelystad virus.

The primary transmission of SIRSV is from animal to animal. Pigs infected with SIRSV shed the virus primarily in oral-nasal secretions. Virus can also be shed in urine and feces. When infected, boars can shed SIRSV in semen and can transmit the virus to susceptible females. Reproductive failure of breeding females, such as abortion, still-births, and weakborn pigs, can persist for 2–3 months within a herd. The herds may have recurrent episodes of clinical signs. Studies indicate that boars initially infected with SIRSV may shed virus in semen for about 35 days, nursery pigs infected with SIRSV may shed for 2–3 months, and pigs infected in utero may shed virus for at least six months after birth.

Swine Infertility and Respiratory Syndrome and Swine Abortion Mortality Syndrome differ in clinical symptoms in that SAMSV-infected swine also exhibit higher abortion rates in all stages of gestation and sow death, in addition to the SIRSV clinical symptoms.

DETAILED DESCRIPTION OF THE INVENTION

The present invention provides a veterinary formulation adapted for inhibiting proliferation of a virus in swine, comprising a compound of formula I, or a physiologically acceptable salt thereof, and a physiologically acceptable carrier. It also provides a method of inhibiting virus proliferation in a swine in need of treatment comprising administering to the swine an effective amount of a compound of formula I or a physiologically acceptable salt thereof.

The term "inhibiting virus proliferation" means preventing the growth or replication and in vivo spread of the virus. The term "in need of treatment" means a swine that is infected by, or has been exposed to, SIRSV, Lelystad virus, or SAMSV. A preferred compound of formula I for use in this invention is tilmicosin, or a physiologically acceptable acid addition salt thereof. A more preferred formula I compound for use in this invention is tilmicosin phosphate.

The term "effective amount" means an amount of formula I compound that is capable of inhibiting SIRSV, Lelystad virus, or SAMSV proliferation in swine. The present veterinary formulations and methods may be used for therapeutic and/or prophylactic treatment, as required. Generally, the specific dose of compound administered to obtain a therapeutic and/or prophylactic effect is not critical. For example, the dose will vary with the compound administered, the identity of the species, the route of administration, and other factors known to those in the field. When the compound is administered via a feed, an effective amount will vary with such particulars as the species, the age, and rate of consumption; however, concentrations in the diet of from about 1 to 4000 ppm will generally provide an effective amount of the compound as a daily dosage. In many situations, diet concentrations in the range of from 100 to 500 ppm will provide efficacy. The compound may also be administered via drinking water at concentrations of about 100 to 300 mg/L.

The veterinary formulations of this invention can be administered by a variety of routes, including oral, rectal, transdermal, subcutaneous, intravenous, intramuscular, and intranasal. A preferred veterinary formulation adapted for inhibiting proliferation of a virus in swine comprises an effective amount of a formula I compound and a standard swine ration. This formulation is particularly useful in controlling SIRSV, Lelystad virus, or SAMSV, which are transmitted from one swine to the next.

The veterinary formulations of this invention are prepared by known procedures, using available ingredients. The formula I compound is typically formulated with one or more physiologically acceptable carriers, such as normal feed components, carriers for injection, and the like.

The following examples are illustrative and are not intended to limit the scope of the invention in any way.

EXAMPLE 1

Tilmicosin Feed Additive Formulations

Formulation I
Tilmicosin Premix, 200 g/kg

| Ingredient | Wt. (g) |
|---|---|
| Tilmicosin Activity | 200 |
| Ground Corn Cobs | 684 |

Formulation II
Tilmicosin Premix, 100 g/kg

| Ingredient | Percent (%) |
|---|---|
| Tilmicosin Premix, 200 g/kg | 50 |
| Rice Hulls | 47 |
| Soybean Oil Refined | 3 |

EXAMPLE 2

In Vivo and in Vitro Effect of Tilmicosin on SIRSV in Swine

Experimental Design

Thirty conventional 8 week-old pigs shown to be SIRSV-free were randomly allocated into four separate groups and treated as follows:

1. 200 ppm of tilmicosin; SIRSV-infected (200, inf)
2. 400 ppm of tilmicosin; SIRSV-infected (400, inf)
3. no treatment; SIRSV-infected (virus)
4. no treatment; no infection (control)

Pigs were treated with either 200 or 400 ppm tilmicosin for 7 days prior to exposure with SIRSV. Treatment was continued after infection. Infected pigs were experimentally infected with the SIRSV isolate VR-2332. Pigs from groups 1, 2, and 3 were infected intranasally with $10^5$ $TCID_{50}$ of the VR-2332 strain of SIRSV, and the pigs from group 4 were left as uninfected controls. The pigs were monitored daily for changes in clinical parameters, body temperature, clinical score of signs, rate of food consumption, and rate of body weight gain. Pigs were euthanized after 14 or 16 days of infection. Blood samples were collected at day 0, 2, 5, 7, 10, 12, and 14 after inoculation. The blood samples were tested for virus isolation (i.e. presence and quantity). Quantity of virus in the blood was determined by a quantitative PCR assay. Virus distribution in tissues was determined by immunocytochemistry and in situ hybridization using virus specific antibodies and probes.

The endpoints for the experiments were the clinical signs, gross and microscopic lesions, viremia, and distribution of virus in infected animals.

Data Analysis

Comparisons were made within animals over time, between animals over the same group, and between groups. For comparison of means of two groups, statistical significance was assessed by Student's test. For comparison of data involving multiple groups, analysis of variance was performed using Systat, a Statistical Analysis System (SAS) package. Significance was always defined as p<0.05.

Results

The following grid outlines the effects of tilmicosin on SIRSV replication in porcine alveolar macrophage. It compares progeny viral yield of alveolar macrophage treated with:

0 μg/mL tilmicosin=A
0.1 μg/mL tilmicosin=B
1.0 μg/mL tilmicosin=C
10 μg/mL tilmicosin=D

| SIRSV Multiplicity of Infection of | | |
|---|---|---|
| 0.1 | 1.0 | 10.0 |
| A > B | A > B | A > B |
| B > C | B > C | B > C |
| C > D | C > D | C > D |
| D = 0 | D = 0 | D = 0 |

Thus, tilmicosin inhibited in vitro replication of the SIRSV virus in alveolar macrophage at all dosages, and completely stopped viral replication at the 10 μg/mL dosage.

Comparison between groups of mean weight gains:

| Day 2 | Day 7 | Day 14 |
|---|---|---|
| control > virus | control > virus | control > virus |
| control < 400, inf | control < 400, inf | control < 400, inf |
| control < 200, inf | control < 200, inf | control < 200, inf |
| virus < 400, inf | virus < 400, inf | virus < 400, inf |
| virus < 200, inf | virus < 200, inf | virus < 200, inf |
| 400, inf > 200, inf | 400, inf > 200, inf | 400, inf > 200, inf |

When comparing means, all infected pigs treated with 440 ppm of tilmicosin gained more weight than the untreated, infected pigs. All infected pigs treated with 200 ppm tilmicosin fared no worse in weight gain than the untreated, infected pigs.

The following grid summarizes the effect of tilmicosin in SIRSV infection, as measured by comparing white blood cell counts from lung lavage:

| White Blood Cell Counts |
|---|
| control < virus |
| control < 400, inf |
| control < 200, inf |
| virus > 400, inf |
| virus > 200, inf |
| 400, inf > 200, inf |

When comparing means, all infected pigs treated with tilmicosin had a lower white blood cell count from lung lavage than the untreated, infected pigs.

The effect of tilmicosin on SIRSV-induced pathology was measured by comparing severity scores of lymph node (LN) hypertrophy:

| Mandibular LN | Tracheobronchial LN | Mediastinal LN |
|---|---|---|
| control < virus | control < virus | control < virus |
| control < 400, inf | control < 400, inf | control < 400, inf |
| control < 200, inf | control < 200, inf | control < 200, inf |
| virus < 400, inf | virus < 400, inf | virus < 400, inf |
| virus < 200, inf | virus < 200, inf | virus < 200, inf |
| 400, inf < 200, inf | 400, inf < 200, inf | 400, inf < 200, inf |

When comparing means, all infected pigs treated with 400 ppm or 200 ppm of tilmicosin had less severe lymph node hypertrophy than the untreated, infected pigs.

The effect of tilmicosin on SIRSV-induced pathology was also measured by comparing severity scores of lung lesions:

| Lung Lesion Severity Scores |
| --- |
| control < virus |
| control < 400, inf |
| control < 200, inf |
| virus > 400, inf |
| virus > 200, inf |
| 400, inf < 200, inf |

When comparing means, all infected pigs treated with 400 ppm or 200 ppm of tilmicosin had less severe lung lesions than the untreated, infected pigs.

I claim:

1. A method of inhibiting viral proliferation in swine in need of treatment comprising administering to the swine an effective dose of an active agent which is a compound of formula I:

wherein

R is a saturated or unsaturated secondary amino group of the formula in which the nitrogen atom is part of an otherwise carbocyclic ring system selected from a monocyclic ring containing from 5 to 16 ring atoms or a bicyclic or tricyclic ring system containing from 8 to 20 ring atoms or such a group wherein one or more of the carbon atoms is substituted by $C_1$–$C_4$ alkyl, $C_2$–$C_4$ alkenyl, $C_2$–$C_4$ alkynyl, $C_1$–$C_4$ alkoxy, $C_1$–$C_4$ alkoxycarbonyl, hydroxyl, $C_1$–$C_4$ alkanoyloxy, halo, halo-$C_1$–$C_4$ alkyl, —N($C_1$–$C_4$ alkyl)$_2$, —N(CH$_2$)$_m$, —C(O)—N($C_1$–$C_4$-alkyl)$_2$,   —C(O)—N(CH$_2$)$_m$, cyano, ethylenedioxy, benzyl, phenyl, or phenyl substituted by from 1 to 3 substituents selected from nitro, halo, $C_1$–$C_4$-alkyl, $C_1$–$C_4$ alkoxy, hydroxy, amino, or mono- or di-($C_1$–$C_4$ alkyl)amino;

m is an integer from 4 through 7;

$R^1$ is a b c $R^2$ is hydrogen; $C_1$–$C_5$-alkanoyl or $C_1$–$C_5$-alkanoyl having from one to three halo substituents; benzoyl, phenylacetyl or phenylpropionyl or benzoyl, phenylacetyl or phenylpropionyl having from one to five halo or methyl or from one to two methoxyl, nitro or hydroxyl substituents;

$R^3$ is hydroxy; $C_1$–$C_5$ alkanoyloxy; $C_1$–$C_5$-alkanoyloxy having from one to three halo substituents; benzoyloxy, phenylacetoxy or phenoxyacetoxy or benzoyloxy, phenylacetoxy or phenoxyacetoxy having from one to five halo or methyl or from one to two methoxyl, nitro or hydroxyl substituents; or or a physiologically acceptable acid addition salt thereof.

2. The method of claim 1 wherein the active agent is tilmicosin or a physiologically acceptable acid addition salt thereof.

3. The method of claim 2 wherein the active agent is tilmicosin phosphate.

4. The method of claim 1 wherein the virus is SIRSV.

5. The method of claim 1 wherein the virus is Lelystad virus.

6. The method of claim 1 wherein the virus is SAMSV.

7. The method of claim 1 wherein the swine to be treated is a boar prior to semen collection.

8. The method of claim 1 wherein the swine to be treated is a breeding female prior to impregnation.

9. The method of claim 1 wherein the swine to be treated is a breeding female during gestation.

10. The method of claim 1 wherein the swine to be treated is a neonatal piglet.

11. A method of decreasing viral load in a swine-producing facility which comprises treating all swine in the facility with an effective dose of a compound of formula I:

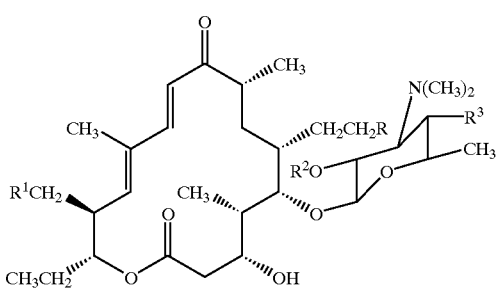

wherein
R is a saturated or unsaturated secondary amino group of the formula

in which the nitrogen atom is part of an otherwise carbocyclic ring system selected from a monocyclic ring containing from 5 to 16 ring atoms or a bicyclic or tricyclic ring system containing from 8 to 20 ring atoms or such a group wherein one or more of the carbon atoms is substituted by $C_1$–$C_4$ alkyl, $C_2$–$C_4$ alkenyl, $C_2$–$C_4$ alkynyl, $C_1$–$C_4$ alkoxy, $C_1$–$C_4$ alkoxycarbonyl, hydroxyl, $C_1$–$C_4$ alkanoyloxy, halo, halo-$C_1$–$C_4$ alkyl, —N($C_1$–$C_4$ alkyl)$_2$, —N(CH$_2$)$_m$,

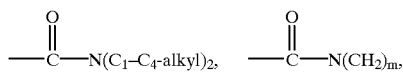

cyano, ethylenedioxy, benzyl, phenyl, or phenyl substituted by from 1 to 3 substituents selected from nitro, halo, $C_1$–$C_4$-alkyl, $C_1$–$C_4$ alkoxy, hydroxy, amino, or mono- or di-($C_1$–$C_4$ alkyl)amino;
m is an integer from 4 through 7;
$R^1$ is

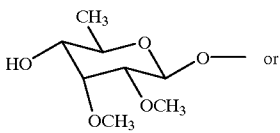

a

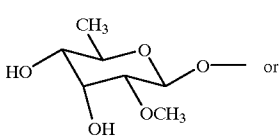

b

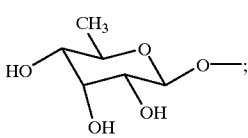

c $R^2$ is hydrogen; $C_1$–$C_5$-alkanoyl or $C_1$–$C_5$-alkanoyl having from one to three halo substituents; benzoyl, phenylacetyl or phenylpropionyl or benzoyl, phenylacetyl or phenylpropionyl having from one to five halo or methyl or from one to two methoxyl, nitro or hydroxyl substituents;

$R^3$ is hydroxy; $C_1$–$C_5$ alkanoyloxy; $C_1$–$C_5$-alkanoyloxy having from one to three halo substituents; benzoyloxy, phenylacetoxy or phenoxyacetoxy or benzoyloxy, phenylacetoxy or phenoxyacetoxy having from one to five halo or methyl or from one to two methoxyl, nitro or hydroxyl substituents; or

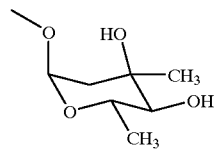

or a physiologically acceptable acid addition salt thereof, for a period of time required to reduce viral load.

12. The method of claim 11 wherein the compound is tilmicosin, or a physiologically acceptable acid addition salt thereof.

13. The method of claim 12 wherein the compound is tilmicosin phosphate.

14. A method of decreasing viral load in a swine-producing facility having both an existing population of swine and newly arriving swine, which comprises treating newly arriving swine before introduction to the existing population with an effective dose of a compound of formula I:

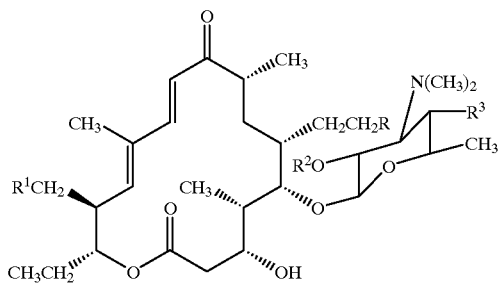

wherein
R is a saturated or unsaturated secondary amino group of the formula

in which the nitrogen atom is part of an otherwise carbocyclic ring system selected from a monocyclic ring containing from 5 to 16 ring atoms or a bicyclic or tricyclic ring system containing from 8 to 20 ring atoms or such a group wherein one or more of the carbon atoms is substituted by $C_1$–$C_4$ alkyl, $C_2$–$C_4$ alkenyl, $C_2$–$C_4$ alkynyl, $C_1$–$C_4$ alkoxy, $C_1$–$C_4$ alkoxycarbonyl, hydroxyl, $C_1$–$C_4$ alkanoyloxy, halo, halo-$C_1$–$C_4$ alkyl, —N($C_1$–$C_4$ alkyl)$_2$, —N(CH$_2$)$_m$,

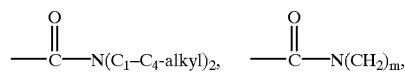

cyano, ethylenedioxy, benzyl, phenyl, or phenyl substituted by from 1 to 3 substituents selected from nitro, halo, $C_1$–$C_4$-alkyl, $C_1$–$C_4$ alkoxy, hydroxy, amino, or mono- or di-($C_1$–$C_4$ alkyl)amino;

m is an integer from 4 through 7;

$R^1$ is

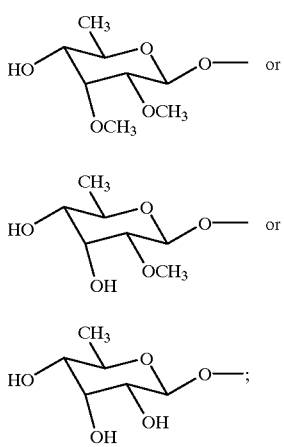

$R^2$ is hydrogen; $C_1$–$C_5$-alkanoyl or $C_1$–$C_5$-alkanoyl having from one to three halo substituents; benzoyl, phenylacetyl or phenylpropionyl or benzoyl, phenylacetyl or phenylpropionyl having from one to five halo or methyl or from one to two methoxyl, nitro or hydroxyl substituents;

$R^3$ is hydroxy; $C_1$–$C_5$ alkanoyloxy; $C_1$–$C_5$-alkanoyloxy having from one to three halo substituents; benzoyloxy, phenylacetoxy or phenoxyacetoxy or benzoyloxy, phenylacetoxy or phenoxyacetoxy having from one to five halo or methyl or from one to two methoxyl, nitro or hydroxyl substituents; or

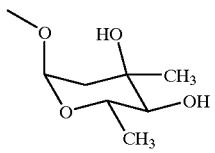

or a physiologically acceptable acid addition salt thereof, for a period of time required to reduce viral load.

15. The method of claim 14 wherein the compound is tilmicosin, or a physiologically acceptable salt thereof.

16. The method of claim 15 wherein the compound is tilmicosin phosphate.

\* \* \* \* \*